United States Patent [19]
Canavan et al.

[11] Patent Number: 5,617,588
[45] Date of Patent: Apr. 8, 1997

[54] SNAP TOGETHER PROTECTIVE GOGGLE CONSTRUCTION WITH TORIC LENS

[75] Inventors: Richard W. Canavan, East Woodstock, Conn.; John G. Mathews, Providence, R.I.

[73] Assignee: Uvex Safety, Inc., Smithfield, R.I.

[21] Appl. No.: 405,144

[22] Filed: Mar. 16, 1995

[51] Int. Cl.⁶ .................................................. A61F 9/02
[52] U.S. Cl. ........................ 2/428; 2/431; 2/437; 2/441; 2/452
[58] Field of Search ............................ 2/441, 443, 436, 2/437, 452, 431, 432, 439, 440, 428, 430

[56] References Cited

U.S. PATENT DOCUMENTS

| | | | |
|---|---|---|---|
| 835,828 | 11/1906 | Meyrowitz | 2/437 |
| 3,055,256 | 9/1962 | Andresen, Jr. | 2/428 X |
| 3,671,976 | 6/1972 | Johnson et al. | 2/430 |
| 3,672,750 | 6/1972 | Hagen | 2/430 X |
| 4,087,865 | 5/1978 | Garofalo | 2/428 |
| 4,264,987 | 5/1981 | Runckel | 2/452 X |
| 4,674,851 | 6/1987 | Jannard . | |
| 4,689,837 | 9/1987 | Bolle | 2/428 X |
| 4,730,915 | 3/1988 | Jannard . | |
| 4,867,550 | 9/1989 | Jannard . | |
| 5,027,443 | 7/1991 | Watkins | 2/441 X |
| 5,181,280 | 1/1993 | Zachry, Jr. | 2/452 |

*Primary Examiner*—Peter Nerbun
*Attorney, Agent, or Firm*—Salter & Michaelson

[57] ABSTRACT

A protective goggle construction consists of a goggle body and a toric lens which is snap received over the front of the goggle body. The goggle body includes a rigid frame portion, and a resilient face engaging portion. The frame portion includes rigid top, bottom and side walls which cooperate to define a goggle interior. The lens includes an optical toric front wall, and further includes top, bottom and side walls extending rearwardly from a peripheral edge of the front wall thereof. The top wall of the lens includes an upstanding ridge formed along the entire length thereof. The face engaging portion includes convex bulges in the temple engaging areas thereof. The rearwardly extending walls of the lens are slidably received over the frame walls to form the assembled goggle construction. Interengaging detent and clip structures are provided on the side walls of the frame and lens to releasably secure the lens and frame in assembled relation. Rearwardly extending ridges on the top and bottom walls of the frame portion cooperate with lens walls to define ventilation passages for providing an air flow over the inner surface of the front lens wall.

20 Claims, 5 Drawing Sheets

SNAP TOGETHER PROTECTIVE GOGGLE CONSTRUCTION WITH TORIC LENS

BACKGROUND AND SUMMARY OF THE INVENTION

The instant invention relates to protective eyewear, and more particularly to a ballistic impact and/or splash resistant protective goggle construction.

Protective eyewear, and more particularly, safety goggles have heretofore been known in the art. However, prior art goggle designs have, in general, been found to be deficient in the following areas: providing a single size goggle body which conforms to both narrow and wide faces; providing adequate ventilation to prevent fogging of the lens while also providing resistance against the entry of liquid materials into the interior of the goggle; and providing a simple mechanism to releasably secure a lens to the goggle body. Prior art safety goggles have also been found to be uncomfortable to wear and poor fitting, thus increasing the likelihood that persons may not wear the goggles, and thus may not receive the impact and splash protection required.

The instant invention provides a goggle construction comprising a goggle body and a corresponding lens which is snap received over the front of the goggle body. The goggle body includes a rigid frame portion for maintaining the shape of the goggle body, and a resilient face engaging portion. The frame portion includes rigid top, bottom and side walls which cooperate to define a goggle interior. The resilient face engaging portion provides a comfortable engaging fit all around the face, and in particular includes convex bulges in the temple engaging areas to provide an engaging fit on both narrow and wide faces. The face engaging portion also provides a shaped nasal area designed to fit comfortably and securely on various shaped faces, e.g., different ethnic faces. The lens includes an optical, toric front wall, and further includes top, bottom and side walls which extend rearwardly from a peripheral edge of the front wall thereof. The lens further includes an upstanding ridge formed along the entire length of the rear peripheral edge of the top wall thereof to provide additional protection from high mass impacts and splashes. The rearwardly extending walls of the lens are slidably received over the goggle body frame walls to form an assembled goggle construction. The side walls of the frame and lens are provided with interengaging detent and clip structures to releasably secure the lens and frame portion in assembled relation. Ridge structures on the top and bottom walls of the frame portion cooperate with top and bottom lens walls to define indirect ventilation passages into the interior of the goggle for providing an air flow over the inner surface of the lens front wall. Since the rearwardly extending lens walls overly the goggle frame walls, splashed or spilled liquids are substantially prevented from entering into the goggle interior through the ventilation passages. A detent and notch arrangement is provided in the nose receiving area for maintaining the frame portion and lens in proper registry. Adjustable strap receiving members are provided on the side walls of the goggle body frame portion for adjustably receiving and securing a strap.

Accordingly, among the objects of the instant invention are: the provision of a safety goggle construction which is comfortable to wear and which will fit both narrow and wide faces; the provision of a safety goggle construction which has adequate air flow over the interior surface of the goggle lens to substantially reduce fogging thereof; the provision of a safety goggle construction which essentially prevents the entry of splashed or sprayed liquids into the interior of the goggle construction; and the provision of a safety goggle construction having a strap receiving member which is easily adjustable.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
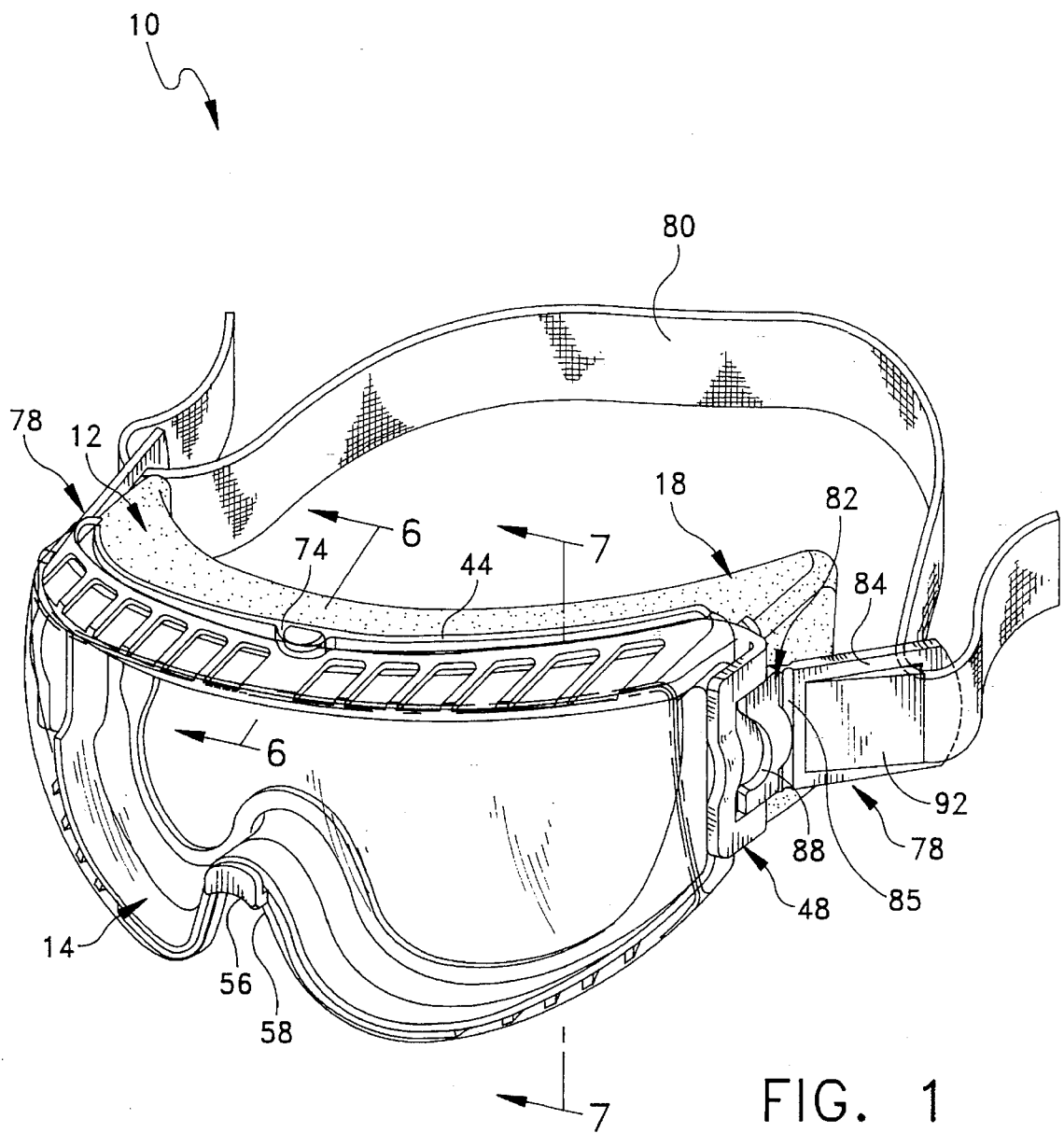
FIG. 1 is a perspective view of the goggle construction of the instant invention.
Figure 2:
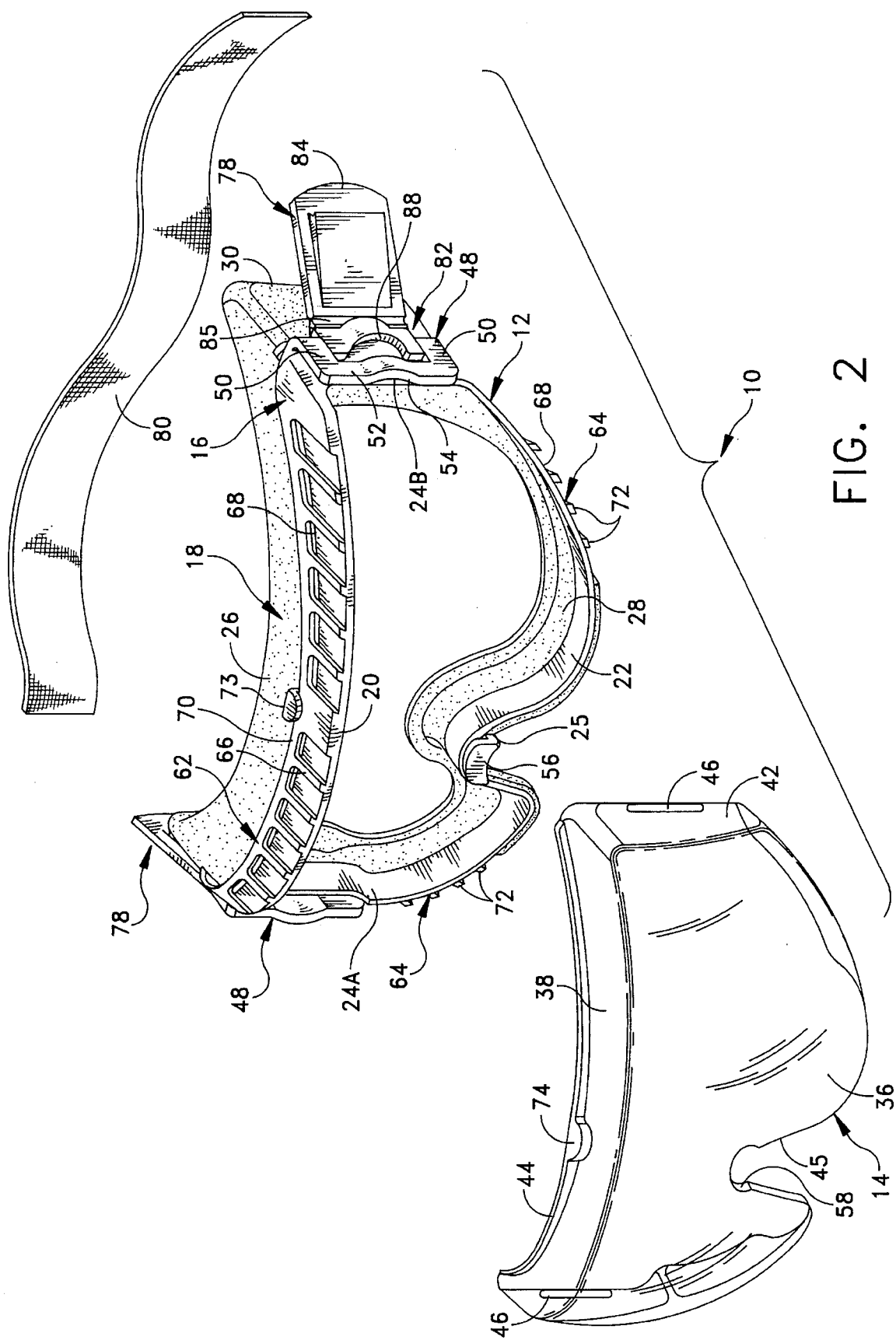
FIG. 2 is an exploded assembly view thereof.
Figure 3:
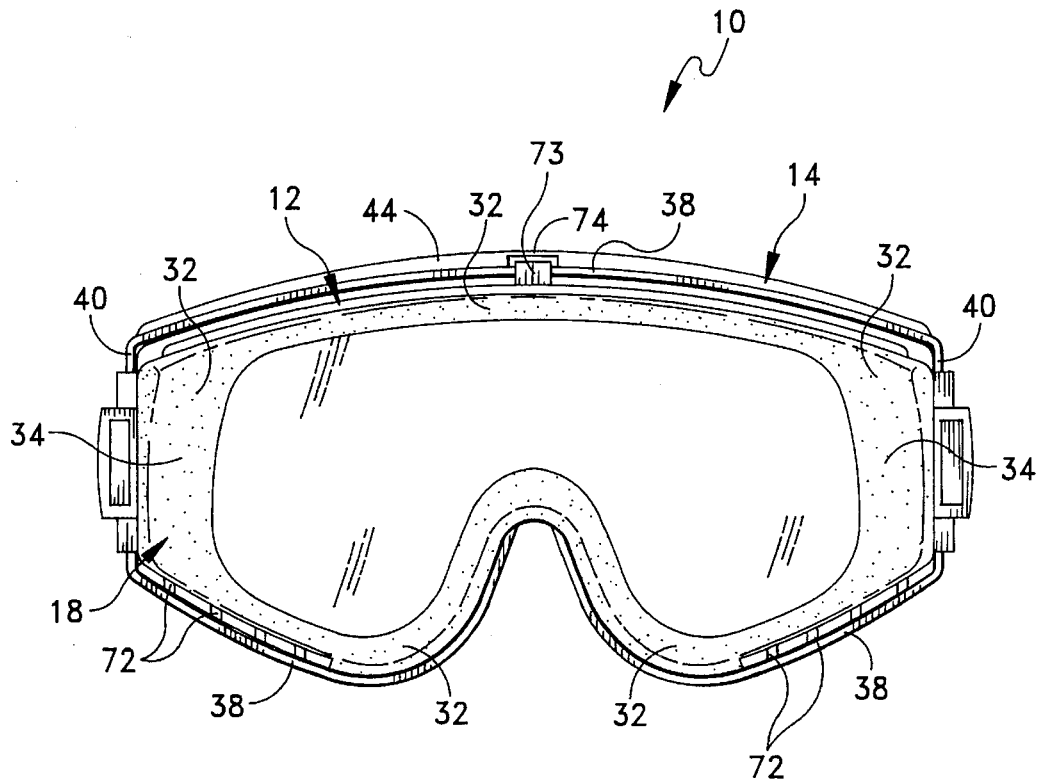
FIG. 3 is a rear view of the goggle body thereof.
Figure 4:
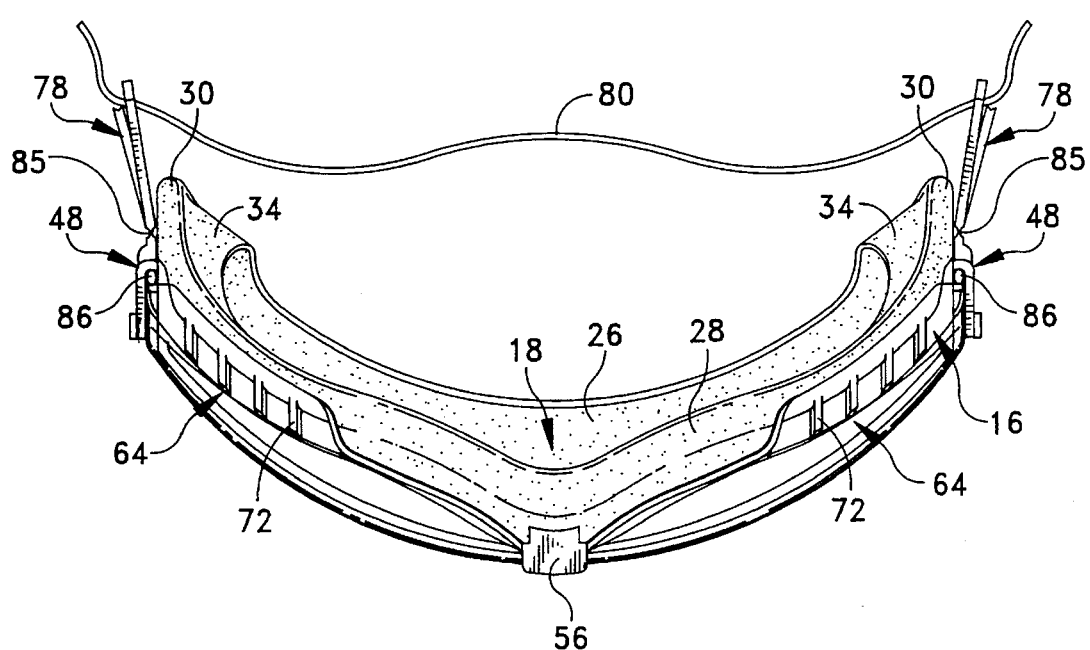
FIG. 4 is a bottom view of the goggle body.
Figure 5:
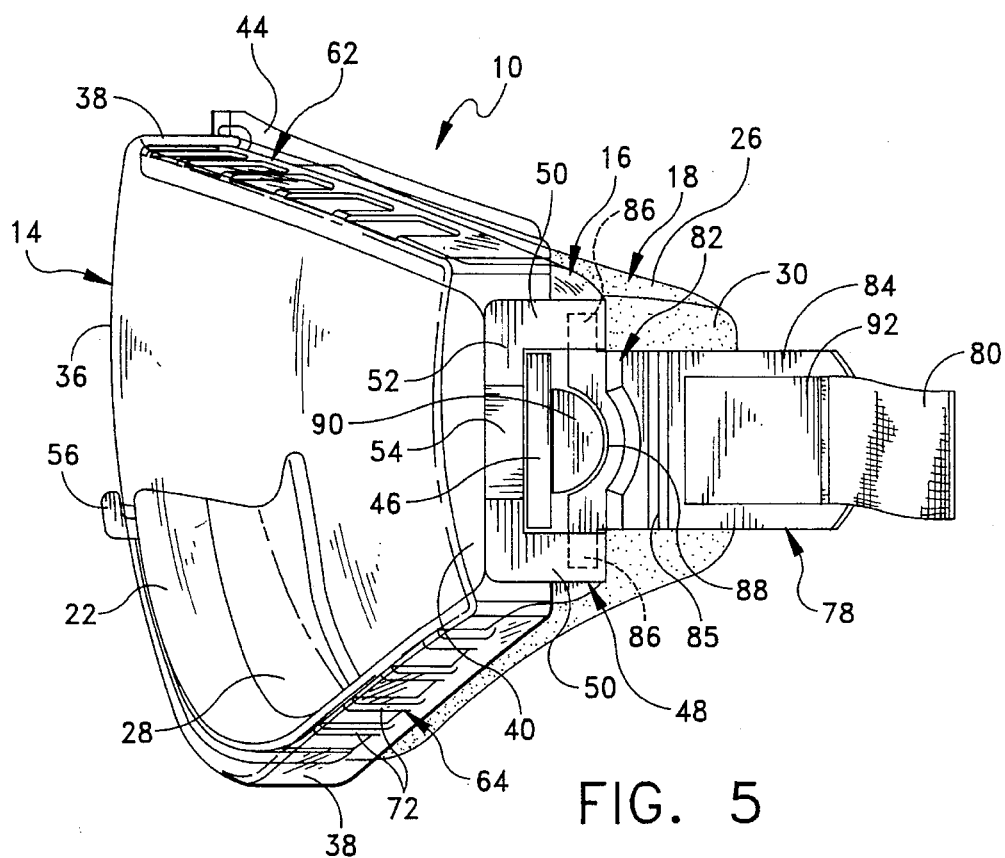
FIG. 5 is a side view of the goggle construction.
Figure 6:
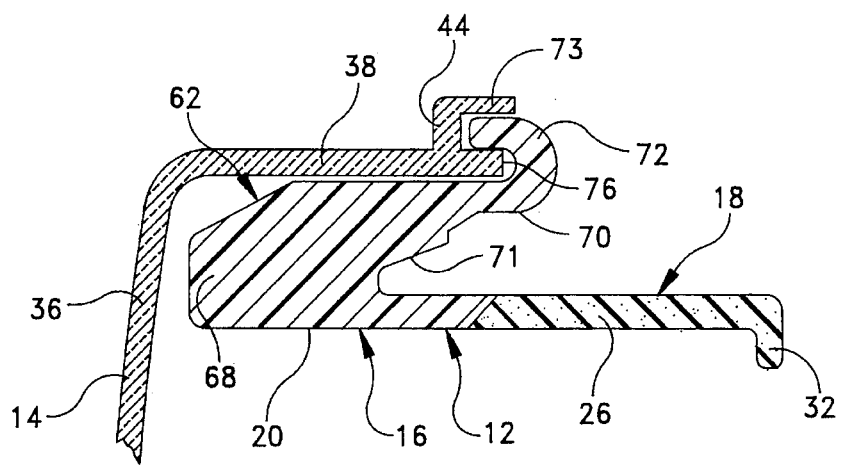
FIG. 6 is a cross-sectional view of the goggle construction, taken along line 6—6 of FIG. 1.

Referring now to the drawings, the safety goggle construction of the instant invention is illustrated and generally indicated at 10 in FIGS. 1–8. As will hereinafter be more fully described, the instant goggle construction 10 comprises a goggle body 12, and a transparent lens 14 which is snap received over the front of the goggle body 12.

The goggle body 12 includes a rigid frame portion generally indicated at 16 for maintaining the shape of the goggle body 10 and a resilient face engaging portion generally indicated at 18. The rigid frame portion 16 is preferably formed from a rigid plastic material such as nylon or polypropylene, and includes top, bottom and side walls 20, 22, and 24A, 24B, respectively, which cooperate to define a goggle interior. The central portion of the bottom wall 22 includes a nose receiving area 25. The resilient face engaging portion 18 is preferably formed from a soft pliable material, such as thermoplastic rubber, and includes top, bottom and side walls 26, 28, and 30 respectively. The peripheral edges of each of the top, bottom and side walls 26, 28, 30 roll inwardly to form flat surfaces 32 (FIG. 3) to engage the forehead, temple, cheek and nose areas of the wearer's face. The temple engaging areas preferably include inwardly facing convex bulges 34 (FIGS. 3 and 4) which are effective for providing a comfortable engaging fit on both narrow and wide faces. The bulge feature 34 on the temple engaging area thus permits the goggle 10 to be manufactured in one size to fit all types of faces.

The rigid frame portion 16 and resilient face engaging portion 18 are preferably integrally formed using a two-shot injection molding process wherein both the hard plastic and soft rubbery material are sequentially injected into the same mold. Two-shot injection molding processes are known in the art, and thus will not be described in detail. During curing of the rigid plastic and rubbery materials in the two-shot molding process, a chemical bond is formed at the junction of the two materials, thereby permanently bonding the two materials together. This type of molding process provides for ease of manufacture, and further provides a long lasting construction.

The lens 14 is preferably molded from a rigid, transparent plastic, such as polycarbonate, and comprises a toric shaped, optical, front wall 36, and top, bottom and side walls 38, 40 and 42, respectively, which extend rearwardly from the peripheral edge of the front wall 36. The polycarbonate material which forms the lens is very ductile and provides effective protection against high mass, i.e., ballistic, impacts to the front wall 36. It is also noted that the lens material may be tinted or coated for reasons that pertain to control of the light spectrum for various tasks. The top wall 38 includes an upstanding ridge 44 extending along its entire rear peripheral edge. The ridge 44 functions to reduce the entry of splashed liquids into the top of the goggle structure and provides additional protection from high mass impacts. The lens 14 further includes a nose receiving area 45.

As illustrated in the drawings, the lens 14 is received in interfitting engagement with the goggle body 12 wherein the rearwardly extending top, bottom and side walls 38, 40, 42 of the lens 14 are slidably received in overlying relation with the top, bottom and side walls 20, 22, 24A and 24B of the goggle frame portion 16 to form the assembled goggle construction.

In order to maintain the lens 14 in assembled relation with the goggle body 12, the side walls 42 of the lens 14 and the side walls 24 of the frame portion 16 are provided with snap received interengaging formations. More specifically, the interengaging formations comprise an outwardly facing detent 46 on the side walls 42 of the lens 14, and a U-shaped clip formation generally indicated at 48 extending outwardly from the side wall 24 of the frame portion 16. The detent 46 and clip formation 48 are most clearly shown in FIGS. 2 and 5. The clip formation 48 comprises two parallel arm portions 50 and a connecting end portion 52. The arms 50 of the clip formation 48 are integrally formed with the side wall 24 and provide a limited degree of flex with respect to the rigid frame portion 16 so that the clip formation 48 can be flexed outwardly to receive the lens detent 46. In use, the detent 46 of the lens 14 engages with an inner edge portion of the connecting end 52 (See FIG. 5). The connecting end portion 52 is formed with a slight outward bow 54 to facilitate grasping of the clip formation 48 to assemble or disassemble the lens 14.

The goggle construction 10 further comprises means for maintaining the lens 14 in registry with the goggle body 12. In this connection, the registry means comprises interengaging formations located in corresponding nose receiving areas 25 and 45 of the goggle body 12 and lens 14. More specifically, the frame portion 16 of the goggle body 12 includes a detent 56 at an apex of the nose receiving area 25, and the lens 14 includes a corresponding notch 58 at the apex of the nose receiving area 45. When the lens 14 is assembled with the goggle body 12, the notch 58 is received over the detent 56 (see FIG. 1).

Figure 7:
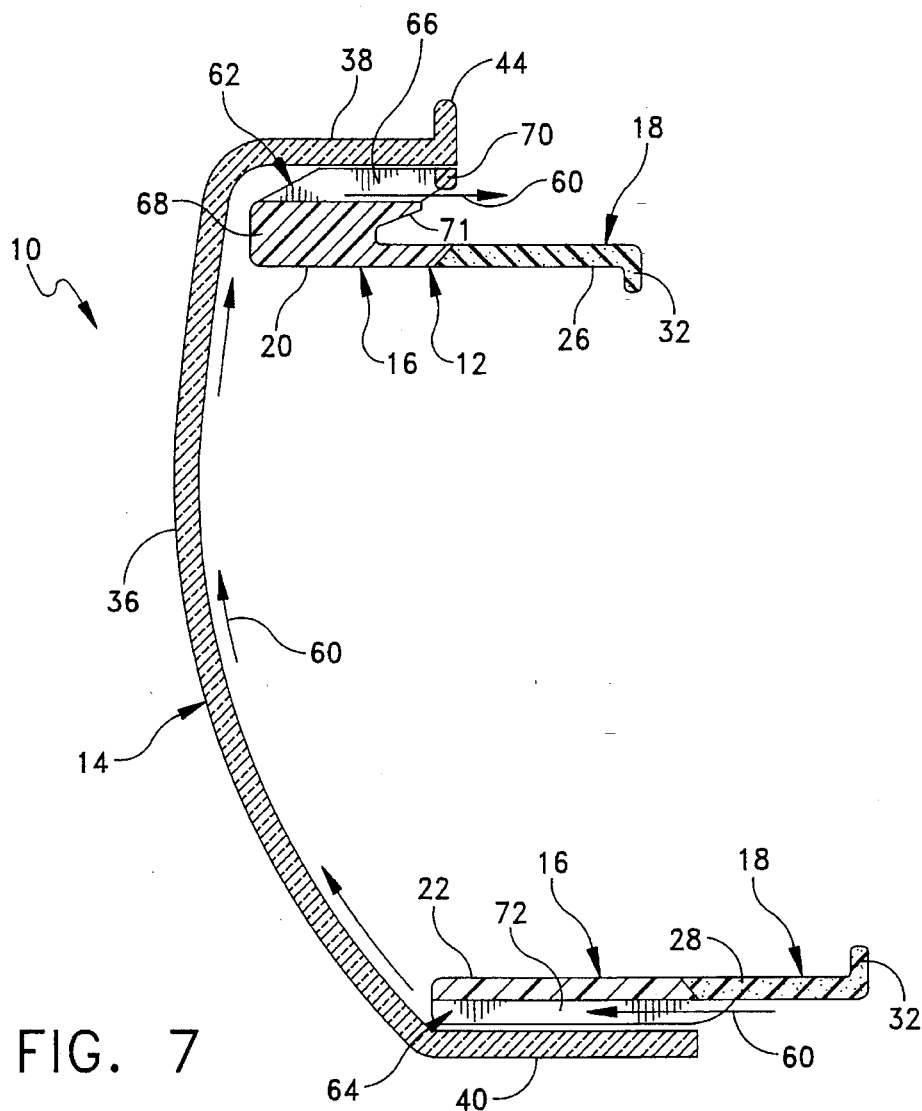
FIG. 7 is a cross-sectional view thereof, taken along line 7—7 of FIG. 1.

The goggle construction 10 still further comprises upper ventilation passages (FIG. 7) in the forehead area adjacent the top wall 20 of the goggle frame 16 and lower ventilation passages in the cheek receiving areas adjacent the bottom wall 22 of the goggle frame 16. The upper and lower ventilation passages cooperate to provide a bottom to top air flow (arrows 60) over the inner surface of the lens front wall 36 to prevent fogging thereof. The top ventilation passages are preferably formed by a ridge structure generally indicated at 62 (FIG. 2) located on the top wall 20 of the frame portion 16. The lower ventilation passages are formed by ridge structures generally indicated at 64 in the cheek receiving areas on the bottom wall 22. The upper ridge structure 62 includes a plurality of spaced ridges 66 which are formed on top of an enlargement 68 on the top wall 20 and extend rearwardly therefrom. The terminal edges of the ridges 66 are connected together by a stabilizing portion 70. The enlargement 68 includes an undercut groove or gutter 71 which is operative for channeling liquids to the sides of the goggle 10 in the event of a splash over the top of the lens 14. It is noted that the upper wall 38 of lens 14 tightly engages the ridges 66 and stabilizing bar 70 to prevent the entry of liquids into the goggle at the juncture thereof. The lower ridge structures 64 each include a plurality of spaced ridges 72 which are formed directly on top of bottom wall 22. The lower spaced ridges 72 actually comprise forwardly extending finger portions of the resilient lower wall 28 of the face engaging portion 18. As illustrated in FIG. 7, the ridge structures 62, 64 cooperate with the lens walls 38, 40 to form ventilation passages wherein the air (arrows 60) passes in front of frame walls 20, 22 and 24, over the top of the enlargements 68 in the spaces created between the ridges 66. The stabilizing portion 70 is provided with a reversely bent tab 73. The tab 73 interfittingly engages with a slot formed by an overturned portion 74 of the lens ridge 44 and a cut out 76 in the rear peripheral edge of the top wall 38 of the lens 14. The tab 73 further maintains the lens 14 in registry with the goggle body 12.

Figure 9:
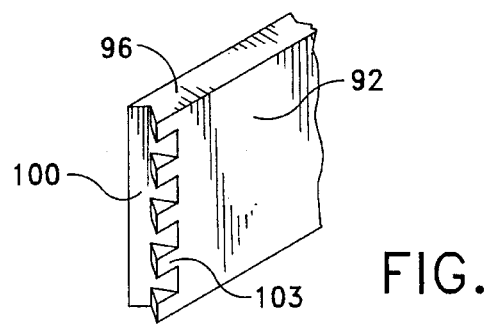
FIG. 9 is a fragmentary perspective view of grasping teeth on the tab of the strap receiving member.
Figure 8:
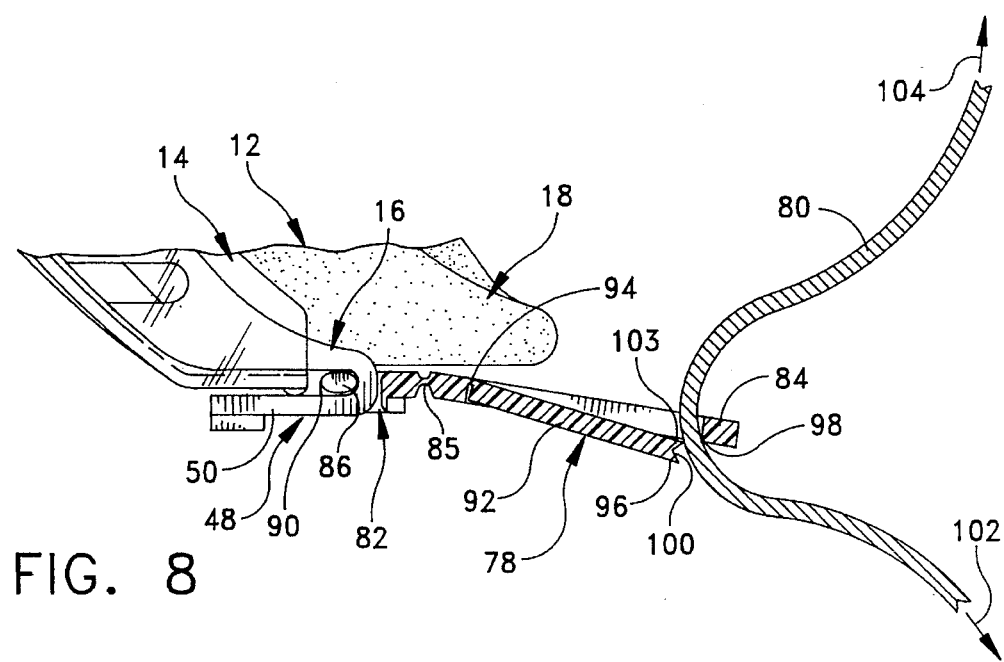
FIG. 8 is an enlarged fragmented view, with the strap receiving member shown partially in cross-section.

The goggle construction 10 further yet comprises a pair of strap receiving members generally indicated at 78 for attaching an elastic strap 80 to the goggle body 12. The strap receiving members 78 are preferably molded from a rigid plastic, such as nylon or polypropylene. The strap receiving members 78 are most clearly illustrated in FIGS. 2 and 5 wherein each of the strap receiving members 78 comprises a body portion generally indicated at 82 and a rearwardly extending planar tab portion 84 connected to the body portion 82 by means of a living hinge 85. The body portion 82 is mounted to the clip formation 48 on the side wall 24 of the frame portion 16 by means of upper and lower pins 86. The hemispherical detent 90 also prevents the lens 14 from pushing too far back. The pins 86 are received in the reverse bends of the arm portions 50 as illustrated in the drawings. The front edge of the body portion 82 is formed with an arcuate surface 88 which interfittingly engages with a hemispherical detent 90 on the side wall 24 of the frame 16. The arcuate surface 88 and hemispherical detent 90 locate and position the strap receiving member 78, and the living hinge 85 permits hinge-like movement of the tab portion 84 with respect to the body portion 82. The tab portion 84 includes a rectangular flap 92 formed therein which is connected to the tab 84 at a front end thereof by a living hinge 94 formed adjacent the inner surfaces of the tab 84 and flap 92. The terminal end 96 of the flap engages with a rearward edge 98 of the tab opening formed by the flap 92. The flap 92 is pushed outwardly through the tab opening so that the inner surface of the terminal edge 96 of the flap 92 engages with the outer surface of the tab 84 adjacent the rearward edge opening 98 (See FIGS. 2, 4, and 8). In use, the strap 80 is extended through the tab opening as illustrated in FIG. 8. Referring to FIGS. 8 and 9, the terminal edge 96 of the flap further includes a v-shaped groove 100 which permits the strap 80 to move freely when pulled outwardly (arrow 102).

However, teeth 103 (FIG. 9) firmly grasp the strap 80 against movement in the inward direction (arrow 104). Loosening of the strap 80 is accomplished by pushing the flap 92 outward to move the terminal edge 96 out of engagement with the strap 80. In addition to the stated features, the living hinge 85 of the strap receiving member 78 provides an improved fit when used in conjunction with hard hats or helmets.

It can therefore be seen that the instant invention provides a unique and novel snap together safety goggle construction 10 which effectively prevents the entry of the splashed liquids into the interior of the goggle while also providing ballistic impact protection and adequate ventilation to prevent fogging of the goggle lens 14. The goggle body 12 is formed by a two-shot injection process to provide an integral hard/soft body wherein the hard and soft portions are chemically bonded together. This unique construction provides superior connection strength and ease of manufacturing. The face engaging portion 18 is molded with convex bulges 34 in the temple engaging areas to provide a comfortable engaging fit on both narrow and wide faces. The goggle 10 can therefore be manufactured in one size which fits all size and shape faces. Unlike prior art designs, the lens 14 snaps over the front of the goggle body 12 to provide easy assembly and replacement of the lens. Since the rearwardly extending lens walls overly the frame walls and ventilation structures 62, 64, splashed or sprayed liquids are substantially prevented from entering into the goggle interior through the ventilation passages. The enlargements 68 on the top wall 20 of the frame portion 16 effectively form a dike to further prevent splashed liquids from running into the interior of the goggle. The strap receiving members 78 provide a simple adjustment means for adjusting the strap length while the goggle 10 is being worn. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

We claim:

1. A goggle construction comprising:

a body including a rigid frame portion, and a resilient elastomeric face engaging portion, said frame portion including a top wall, a bottom wall and side walls which cooperate to define a unitary goggle interior which encloses both eyes of a user, said face engaging portion including a top wall, a bottom wall and side walls which depend from and cooperate with said top wall, bottom wall and side wall portions of said frame portion to further define said goggle interior;

a lens including a front wall, and further including top, bottom and side walls extending rearwardly from a peripheral edge of the front wall thereof, said lens being received in interfitting engagement with said body wherein said top, bottom and side walls of said lens are slidably received in overlying relation with said top, said bottom and said side walls of said frame portion; and means for releasably securing said lens in interfitting engagement with said frame portion.

2. In the goggle construction of claim 1, said means for releasably securing said lens in interfitting engagement with said body comprising corresponding interengaging formations located on the side walls of said frame portion and the side walls of said lens.

3. In the goggle construction of claim 2, said interengaging formations comprising an outwardly facing detent formed on said side wall of said lens and a U-shaped resilient clip formation extending outwardly from an outer surface of said side wall of said frame portion, said clip formation having a terminal edge which engages with said detent.

4. The goggle construction of claim 1 further comprising means for maintaining said lens in registry with said frame portion.

5. In the goggle construction of claim 4, said means for maintaining said lens in registry with said frame portion comprising interengaging formations located in corresponding nose receiving areas of said frame portion and said lens.

6. In the goggle construction of claim 5, said interengaging formations comprising a detent at an apex of the nose receiving area of said frame portion, and a corresponding slot in an apex of the nose receiving area of said lens.

7. The goggle construction of claim 1 further comprising a pair of strap receiving members respectively mounted to the side walls of said frame portion.

8. In the goggle construction of claim 7, each of said strap receiving member comprising a tab having a forward portion thereof mounted to the side wall of the frame portion, and further comprising a flap having a forward edge hingeably connected to said tab along a substantially vertical axis, said flap further having a terminal edge which engages with a corresponding inner edge of said tab.

9. In the goggle construction of claim 8, said tab and said flap having inner and outer surfaces, said tab and said flap being connected by a living hinge formed adjacent the inner surfaces thereof, said inner surface of said terminal edge of said flap engaging said outer surface of said tab.

10. In the goggle construction of claim 9, said terminal edge of said flap tapering to a blade adjacent said inner surface thereof.

11. The goggle construction of claim 8 further comprising means for hingeably mounting said forward portion of said tab to said frame portion of said body.

12. In the goggle construction of claim 1, said face engaging portion being integrally formed with said rigid frame portion wherein said rigid frame portion and said face engaging portion have a direct chemical bond therebetween.

13. In the goggle construction of claim 1, said top, bottom and sidewalls of said face engaging portion each including an end portion which rolls inwardly to form respective flat face engaging surfaces, said face engaging surfaces including temple engaging area, said temple engaging areas including inwardly extending convex bulges.

14. A goggle construction comprising:

a body including a rigid frame portion, and a resilient elastomeric face engaging portion, said frame portion including a top wall, a bottom wall and side walls which cooperate to define a unitary goggle interior which encloses both eyes of a wearer, said face engaging portion including a top wall, a bottom wall and side walls which depend from and cooperate with said top wall, bottom wall and side wall portions of said frame portion to further define said goggle interior;

a lens including a front wall, and further including top, bottom and side walls extending rearwardly from a peripheral edge of the front wall thereof, said lens being received in interfitting engagement with said body wherein said top, bottom and side walls of said lens are slidably received in overlying relation with said top, said bottom and said side walls of said frame portion;

means for releasably securing said lens in interfitting engagement with said frame portion;

a first ventilation passage adjacent a bottom wall of said lens; and a second ventilation passage adjacent a top wall of said lens, said first and second ventilation passages cooperating to provide an air flow over said front wall of said lens.

15. In the goggle construction of claim 14, said front wall of said lens being maintained in closely spaced relation to forward edges of said top and bottom walls of said frame portion of said goggle body, said top and bottom walls of said frame including a plurality of rearwardly extending spaced ridges, said ridges cooperating with said top and bottom wall of said lens to define top and bottom ventilation passages into said goggle interior, said ventilation passages cooperating to provide an air flow over an interior surface of said front wall of said lens.

16. A goggle body construction comprising a rigid frame portion, and a resilient face engaging portion, said face engaging portion including a top wall, a bottom wall and side walls which extend rearwardly and cooperate to define a goggle interior, each of said walls rolling inwardly to form flat face engaging surfaces, said face engaging surfaces including two opposing temple engaging areas, said temple engaging areas each including an inwardly extending convex bulge.

17. A goggle construction comprising:

a body including a rigid frame portion, and a resilient face engaging portion, said frame portion including a top wall, a bottom wall and side walls which cooperate to define a goggle interior;

a lens including a front wall, and further including top, bottom and side walls extending rearwardly from a peripheral edge of the front wall thereof, said lens being received in interfitting engagement with said body wherein said top, bottom and side walls of said lens are slidably received in overlying relation with said top, said bottom and said side walls of said frame portion; and interengaging formations for releasably securing said lens in interfitting engagement with said frame portion, said interengaging formations comprising an outwardly facing detent formed on said side wall of said lens and a U-shaped resilient clip formation extending outwardly from an outer surface of said side wall of said frame portion, said clip formation having a terminal edge which engages with said detent.

18. A goggle construction comprising:

a body including a rigid frame portion, and a resilient face engaging portion, said frame portion including a top wall, a bottom wall and side walls which cooperate to define a goggle interior;

a lens including a front wall, and further including top, bottom and side walls extending rearwardly from a peripheral edge of the front wall thereof, said lens being received in interfitting engagement with said body wherein said top, bottom and side walls of said lens are slidably received in overlying relation with said top, said bottom and said side walls of said frame portion;

means for releasably securing said lens in interfitting engagement with said frame portion; and interengaging formations located in corresponding nose receiving areas of said frame portion and said lens for maintaining said lens in registry with said frame portion.

19. In the goggle construction of claim 18, said interengaging formations comprising a detent at an apex of the nose receiving area of said frame portion, and a corresponding slot in an apex of the nose receiving area of said lens.

20. A goggle construction comprising:

a body including a rigid frame portion, and a resilient face engaging portion, said face engaging portion including rearwardly extending top, bottom and side walls, each of said walls rolling inwardly to form flat face engaging surfaces, said face engaging surfaces including a temple engaging area on each side thereof, said temple engaging areas including inwardly extending convex bulges, said frame portion including a top wall, a bottom wall and side walls which cooperate to define a goggle interior;

a lens including a front wall, and further including top, bottom and side walls extending rearwardly from a peripheral edge of the front wall thereof, said lens being received in interfitting engagement with said body wherein said top, bottom and side walls of said lens are slidably received in overlying relation with said top, said bottom and said side walls of said frame portion; and means for releasably securing said lens in interfitting engagement with said frame portion.

* * * * *